United States Patent [19]

Nagasawa

[11] Patent Number: 4,849,859
[45] Date of Patent: Jul. 18, 1989

[54] LASER-TYPE HANDPIECE

[75] Inventor: Akinori Nagasawa, Omiya, Japan

[73] Assignee: Kabushiki Kaisha Morita Seisakusho, Kyoto, Japan

[21] Appl. No.: 40,923

[22] Filed: Apr. 21, 1987

[30] Foreign Application Priority Data

Apr. 22, 1986 [JP] Japan ............................. 060797[U]
Apr. 22, 1986 [JP] Japan ............................. 060798[U]

[51] Int. Cl.$^4$ ............................................. F21V 8/00
[52] U.S. Cl. .......................................... 362/32; 128/6;
128/303.1; 350/96.1; 362/284; 362/324; 433/114
[58] Field of Search .................. 362/32, 282, 284, 322, 362/324; 350/96.1, 96.24, 96.25, 96.26; 128/4–7, 303.1, 395–398; 433/114; 353/DIG. 3

[56] References Cited

U.S. PATENT DOCUMENTS

| | | | |
|---|---|---|---|
| 2,783,757 | 3/1957 | Scholz | 128/4 |
| 2,859,660 | 11/1958 | Lucas | 353/DIG. 3 X |
| 3,096,756 | 7/1963 | Rosenfeld et al. | 128/6 |
| 3,880,148 | 4/1975 | Kanehia et al. | 128/6 |
| 4,551,129 | 11/1985 | Coleman et al. | 604/21 |
| 4,592,353 | 6/1986 | Daikuzono | 128/303.1 |

FOREIGN PATENT DOCUMENTS

| | | | |
|---|---|---|---|
| 2430148 | 1/1975 | Fed. Rep. of Germany | 350/96.26 |
| 3436508 | 5/1985 | Fed. Rep. of Germany | 128/303.1 |
| 84409 | 9/1935 | Sweden | 362/322 |

Primary Examiner—Martin P. Schwadron
Assistant Examiner—Allen J. Flanigan
Attorney, Agent, or Firm—Koda and Androlia

[57] ABSTRACT

A laser-type handpiece including a reflector pivotably connected inside a head section and a control sleeve which is connected to the reflector and fitted over the external circumference of the handpiece body so that the sleeve can move back-and-forth along the axis of the handpiece body, whereby the reflector can be adjusted to any desired angle by the back-and-forth movement of the sleeve. When this handpiece is used for dental treatment, the head section of the handpiece can be smoothly inserted into and taken out from a narrow oral region and the angle of laser beam can be changed easily.

5 Claims, 7 Drawing Sheets

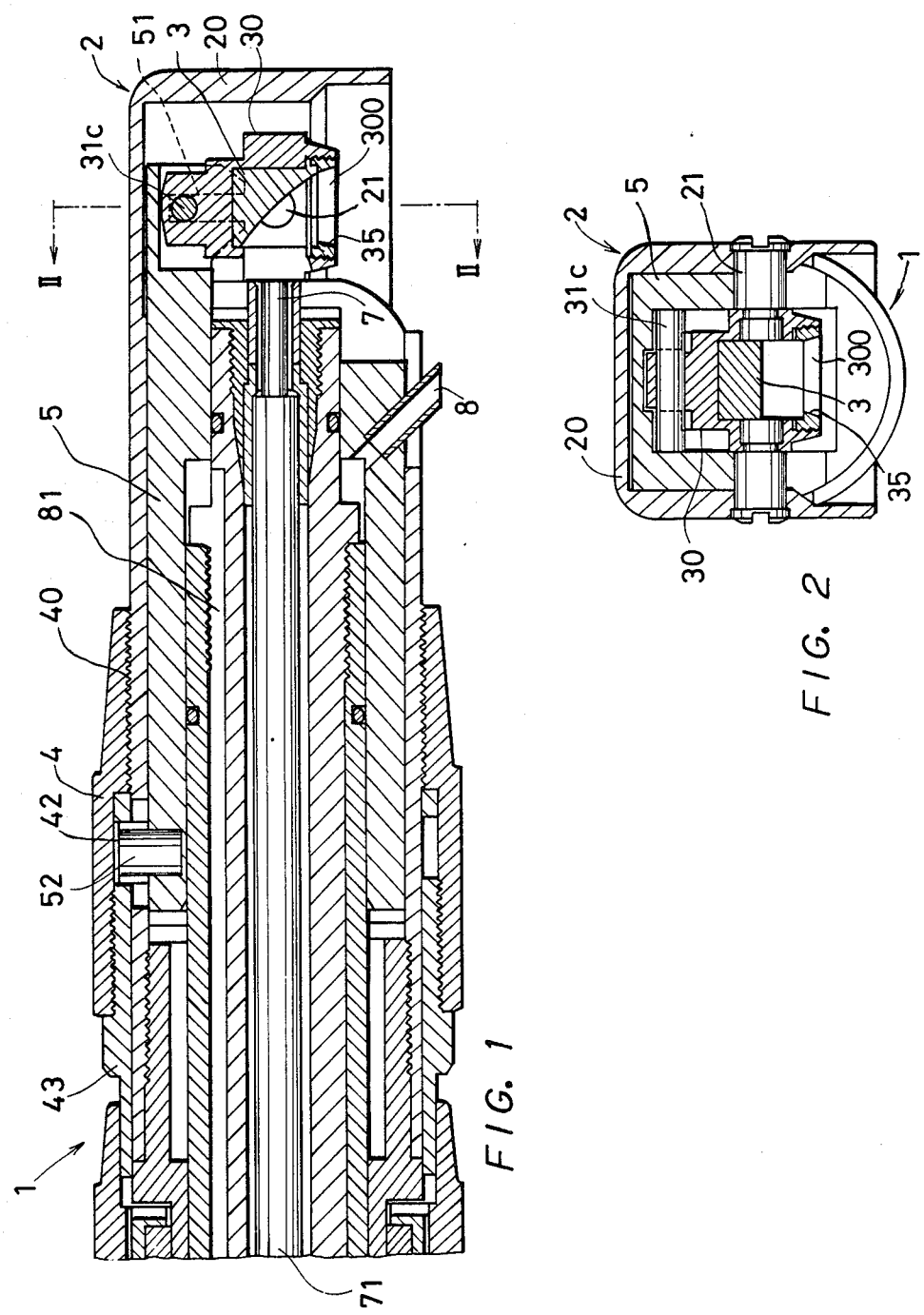

LASER-TYPE HANDPIECE

BACKGROUND OF THE INVENTION

1. Field of the Invention

The present invention relates to a laser-type handpiece to be used for medical treatment, in particular, dental treatment.

2. Prior Art

These days, various attempts have been made to use lasers in the field of medical treatment and some of them are coming into practical use. Japanese Utility Model Publication No. 57-163253 shows an example of a laser applied mainly to a dental handpiece. In this example, a reflector is turned by operating a control knob provided outside the handpiece body so that the laser beam from a laser source is refracted at a desired angle.

In the case of this handpiece, however, a knob protrudes from the head section of the handpiece. When the head section is inserted into a narrow oral region (mouth), the knob is in the way of inserting the head section. In addition, since the knob is directly connected to the shaft of the reflector, the knob must be controlled in the mouth or after taking out the head section from the mouth. Therefore, the handpiece is not easy to use and it is very difficult to accurately aim the laser beam at a target portion.

SUMMARY OF THE INVENTION

It is therefore an object of the present invention to provide a dental handpiece which is easy to use and can accurately aim the laser beam by changing the angle of the reflector using a control sleeve fitted over the handpiece body, i.e. the grip of the handpiece.

Another object of the present invention is to provide a handpiece which is characterized in that a member for holding for example a probe, which is mounted on the head section and is used for contact treatment, is rotatable together with the reflector, and the change in angle of the holding member is approximately twice as large as that of the reflector to make contact treatment possible using lasers.

BRIEF DESCRIPTION OF THE DRAWINGS

FIG. 1 is a vertical partially-sectional view illustrating a basic embodiment of the handpiece of the present invention;

FIG. 2 is a sectional view taken on line II—II of FIG. 1;

DETAILED DESCRIPTION OF THE INVENTION

Figure 3:
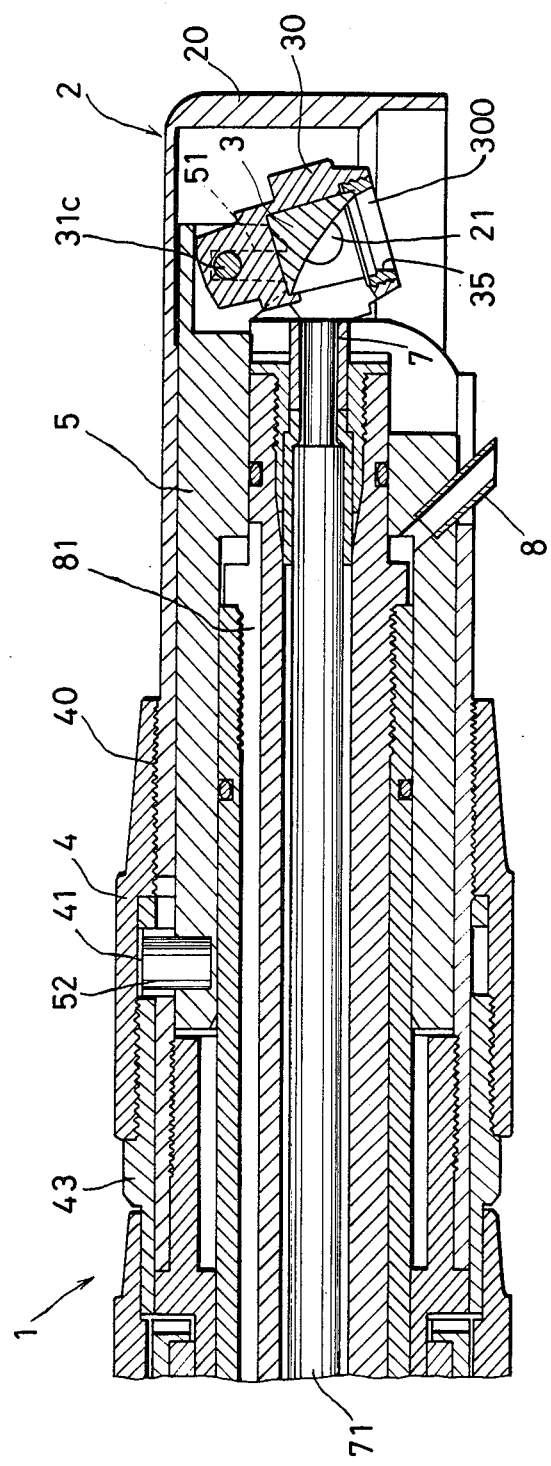
FIG. 3 is a view illustrating an operation condition similar to FIG. 1.

The laser-type handpiece shown in FIGS. 1, 2 and 3 is a basic embodiment of the present invention, wherein laser beam transmitted from a laser source to a handpiece body 1 is refracted at a head section 2, the laser-type handpiece is characterized in that the handpiece comprises a reflector 3 pivotably connected inside the head section 2 and a control sleeve 4 which is fitted over the external circumference of the handpiece body 1 so that the sleeve can move back and forth along the axis of the handpiece body 1 and is connected to the reflector 3, whereby the reflector 3 can be adjusted to any desired angle by the back-and-forth movement of the sleeve 4.

The laser-type handpieces shown in FIGS. 4 to 9 are embodiments similar to the above embodiments. The laser-type handpiece wherein laser beam transmitted from a laser source to the handpiece body 1 is refracted at the head section 2, is characterized in that the handpiece comprises a reflector holding member 30 pivotably connected to the head section 2 via a pivot shaft 21, and an applicator holding member 6 pivotably connected to the head section 2 via the pivot shaft 21. A control sleeve 4 is fitted over the external circumference of the body 1 so that the sleeve 4 can be moved back and forth along the axis of the body 1, and a slide member 5 is connected to the upper section of the reflector holding member 30 and the upper section of the applicator holding member 6 via connection points 31 and 61 respectively and is provided in the body 1 so that the slide member 5 can slide along the axis of the body 1, and is interlocked with the back-and-forth movement of the sleeve 4, whereby the reflector holding member 30 and the applicator holding member 6 are turned around the pivot shaft 21 by sliding the slide member 5 interlocked with the back-and-forth movement of the sleeve 4, and the change in angle of the applicator holding member 6 is approximately twice as large as the change in angle of the reflector holding member 30.

A non-contact contra-angle handpiece embodiment of the present invention is shown in FIGS. 1 to 3. The reflector 3 is held by the reflector holding member 30 and the reflector holding means 30 is pivotably connected to a head housing 20 via the pivot shaft 21. With this structure, the reflector 3 is rotatably supported around the axial center of the pivot shaft 21 in the head section 2.

A pin 31c is fixed in parallel with the pivot shaft 21 at the upper section of the reflector holding member 30. The slide member 5 which slides along the axis of the body 1 is built in the body 1. At the front end of the slide member 5, the pin 31c is fitted into a slot or hole for a shaft (a hole for a shaft is shown) 51 which intersects the axis of the body 1 at right angles. At the rear end of the slide member 5, a protrusion for engagement 52 which intersects the axis of the body 1 is fixed and fitted into a circumferential groove 42 provided on the inner surface of the control sleeve 4.

The sleeve 4 is fitted over external circumference of the handpiece body 1 (grip section) via a threaded section 40. When the sleeve 4 is turned around the threaded section 40, the sleeve 4 can move back and forth along the axis of the body 1. At the rear end of the sleeve 4, the sleeve 4 is fitted over and secured to slide a ring 43 via a threaded section, which ring 43 is installed around the external circumference of the body 1 so that the slide ring 43 can slide back and forth along the axis of the body 1 as the sleeve 4 is moved. The sleeve 4 is not limited to the structure shown in the figures but can be moved back and forth using other methods.

The reflector 3 is prism-shaped as shown in the figures and is held by a ring screw 35 which is installed in an irradiation port 300 provided at the lower section of the reflector holding member 30. Although a concave mirror is used as the reflector 3, a plane mirror can also be used. An optical lens or the like can also be provided between the reflector 3 and an optical fiber 7 when required.

An optical fiber 7 transmits the laser beam. The optical fiber 7 which is covered with a sheath 71 is associated with a laser source (not shown) coaxial with the body 1. The end of the fiber 7 faces the reflector 3 at the head section 2. Numeral 8 designates an outlet from which an active medium such as water required for dental treatment is discharged. The outlet 8 is fixed to the slide member 5 and moves back and forth as the slide member 5 slides. The above-mentioned active medium which is supplied through a supply passage 81 is jetted from the outlet 8 to a treatment portion. At the open space around the optical fiber 7, a gas passage can be provided to cool the treatment portion and the reflector 3 and to prevent the reflector 3 from becoming foggy due to smoke emitted from the treatment portion.

With the handpiece having the above-mentioned structure, when the control sleeve 4 is advanced and retracted along the threaded section 40, the sleeve 4 moves back and forth along the axis of the body 1. The protrusion for engagement 52 which is fixed at the rear end of the slide member 5 is fitted into the circumferential groove 42 provided on the inner surface of the sleeve 4. The pin 31c fixed to the reflector holding member 30 is fitted into the slot 51 provided at the front end of the slide member. Therefore, as the sleeve 4 moves back and forth, the slide member 5 slides in the body 1 along the axis of the body 1 and the reflector holding member 30 turns around the pivot shaft 21. With this structure, the laser beam emitted from the optical fiber 7 is refracted at a desired angle by the reflector 3. Referring to FIG. 1, the laser beam is refracted nearly at a right angle. When the sleeve 4 is turned and retracted as shown in FIG. 3, the pin 31c is pulled backward by the slide member 5 and the reflector 3 turns counterclockwise around the pivot shaft 21 as shown in FIG. 3. It is easily understood according to the above descriptions that the laser beam can be refracted in the opposite direction by moving the sleeve 4 forward.

As described above, in the laser-type handpiece shown in FIGS. 1 to 3, the angle of the reflector 3 pivotably connected to the head section 2 is changed by moving the control sleeve 4 fitted over the external circumference of the handpiece body 1 back and forth along the axis of the body 1. Due to this structure, any members which are used to change the angle of the reflector 3 do not protrude from the external surface of the head section 2. When this system is applied to a dental handpiece, it can be easily inserted into and taken out from a narrow oral region without problems. The irradiation direction of the laser beam can be changed during treatment by operating the sleeve 4 provided away from the head section 2. Therefore, it is not necessary to take out and reinsert the head section 2 each time the angle is changed during dental treatment. As a result, efficient and accurate treatment is ensured. A contact-type contra-angle handpiece of the present invention is shown in FIGS. 4 to 9. The reflector holding member 30 and the applicator holding member 6 are pivotably supported by the head section 2 via the pivot shaft 21 so that they can turn independently around the axis of the pivot shaft 21. Like the non-contact handpiece, the reflector 3 is mounted on the reflector holding member 30 by the ring screw 35. An oval conical treatment contact probe 60 or a condenser lens (not shown) is installed in the applicator holding member 6 via set screws 62 and 63 so that the probe 60 or the lens can be properly aligned with the optical path of the laser beam refracted by the reflector 3.

Like the non-contact handpiece, the control sleeve 4 is fitted over the external circumference of the handpiece body 1 via the thread section 40 so that the sleeve 4 can move back and forth together with the slide ring 43 around the external circumference of the body 1 and along the axis of the body 1 as the sleeve 4 is advanced and retracted along the thread section 40. This back-and-forth movement mechanism is not limited to that shown in FIGS. 4 to 6. Like the non-contact type handpiece, a slide member 5 which slides along the axis of the body 1 is built in the body 1.

Also like the non-contact type handpiece, the slide member 5 is connected to the control sleeve 4 via the protrusion for engagement 52 and the circumferential groove 42 so that the slide member 5 moves back and forth as the sleeve 4 is moved back and forth. The front end of the slide member 5 is connected to the reflector holding member 30 and the applicator holding member 6 via the connection points 31 and 61 respectively. As the slide member 5 is moved, these holding members 30 and 6 turn around the pivot shaft 21. The change of angle of the applicator holding member 6 which is obtained by the turning operation is set twice as large as that of the reflector holding member 30.

Figure 4:
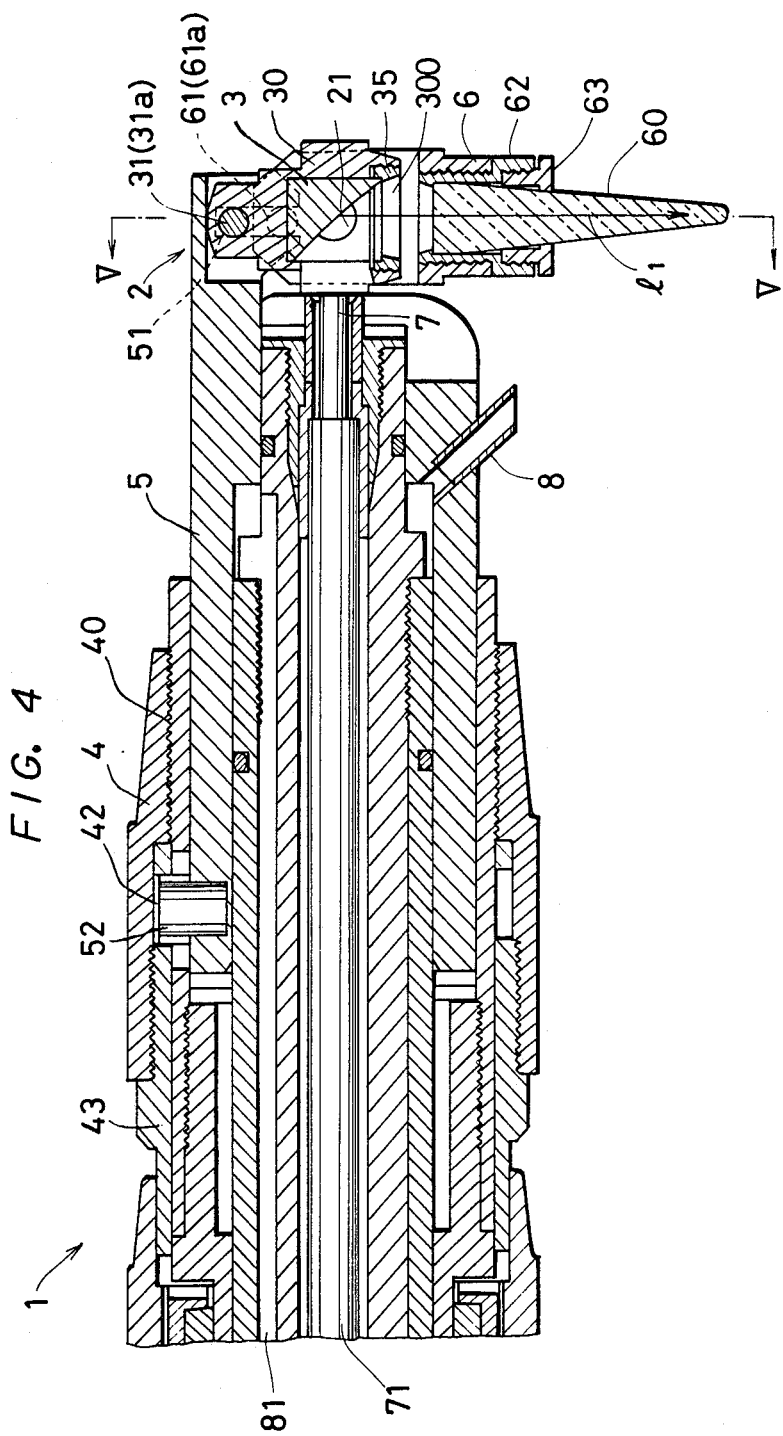
FIG. 4 is a vertical partially-sectional view illustrating a second embodiment.
Figure 5:
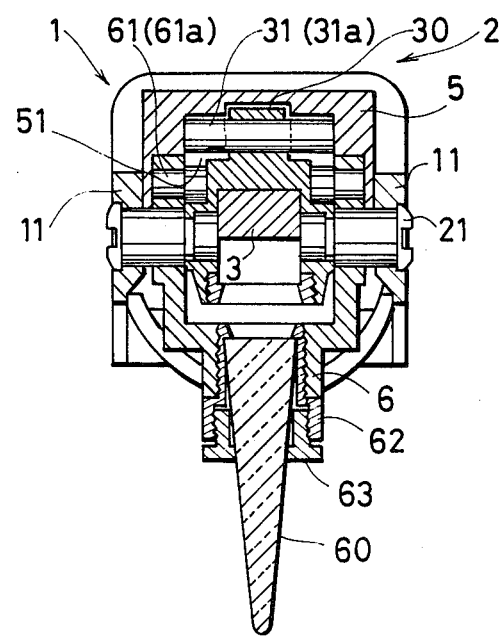
FIG. 5 is a sectional view taken on line V—V of FIG. 4.
Figure 6:
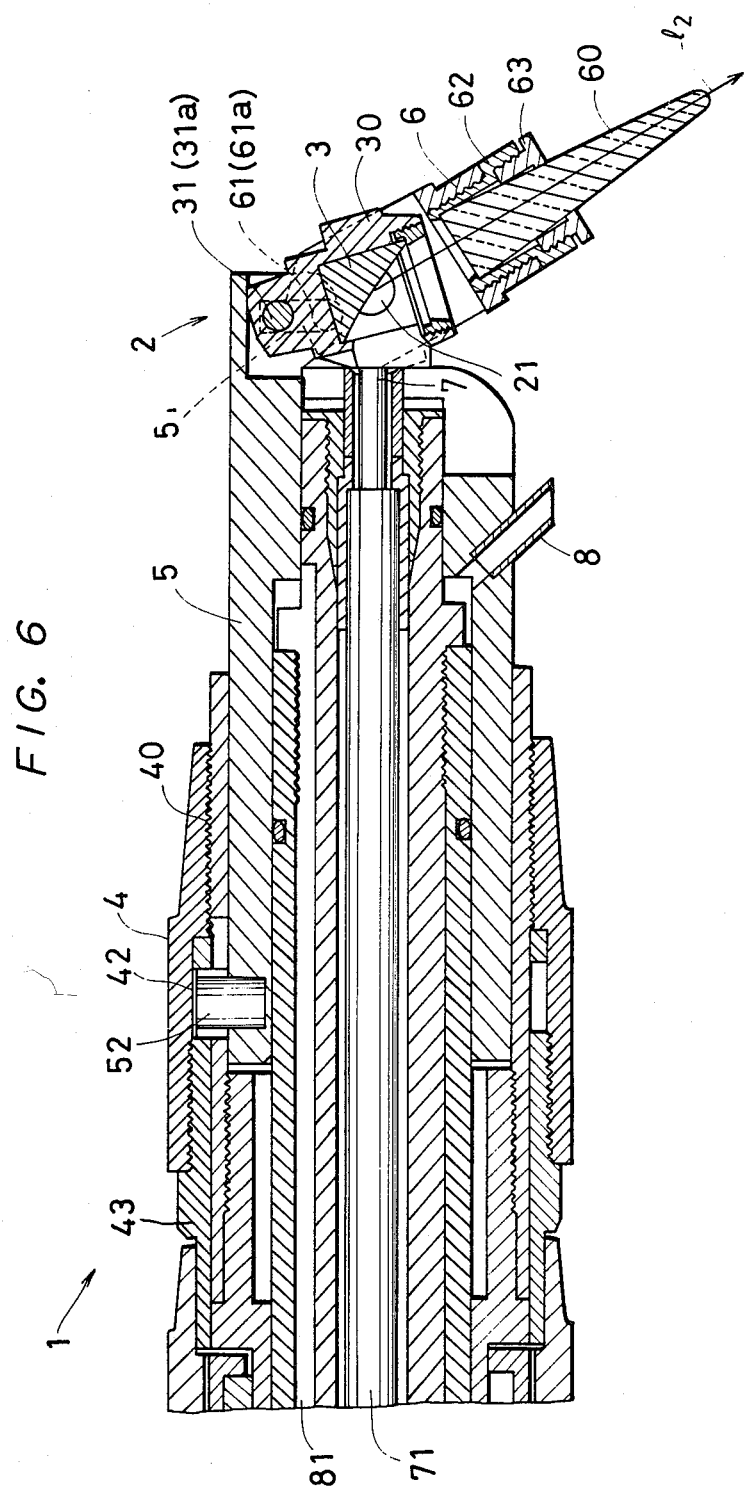
FIG. 6 is a view illustrating an operation condition of the second embodiment and is similar to FIG. 4.
Figure 7:
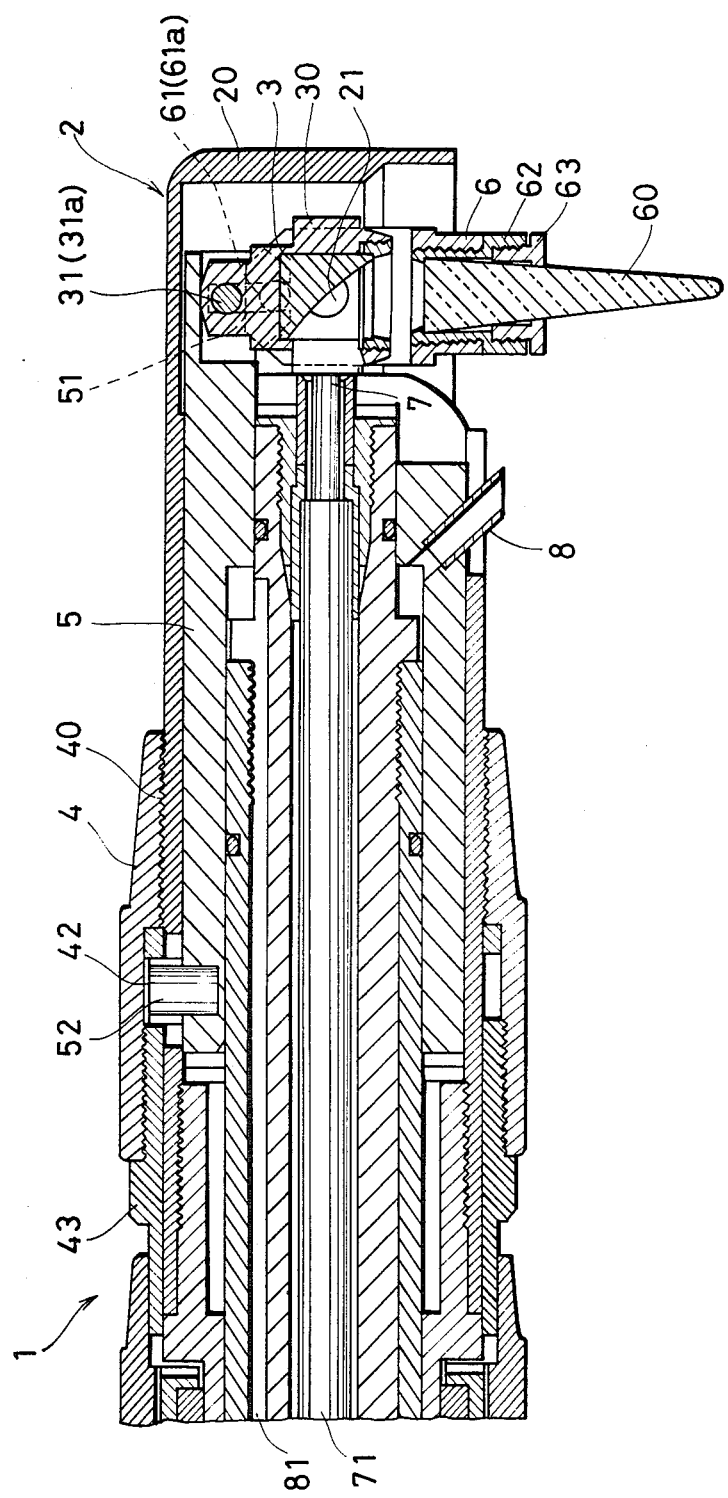
FIG. 7 is a vertical partially-sectional view illustrating a third embodiment similar to FIG. 4.
Figure 8:
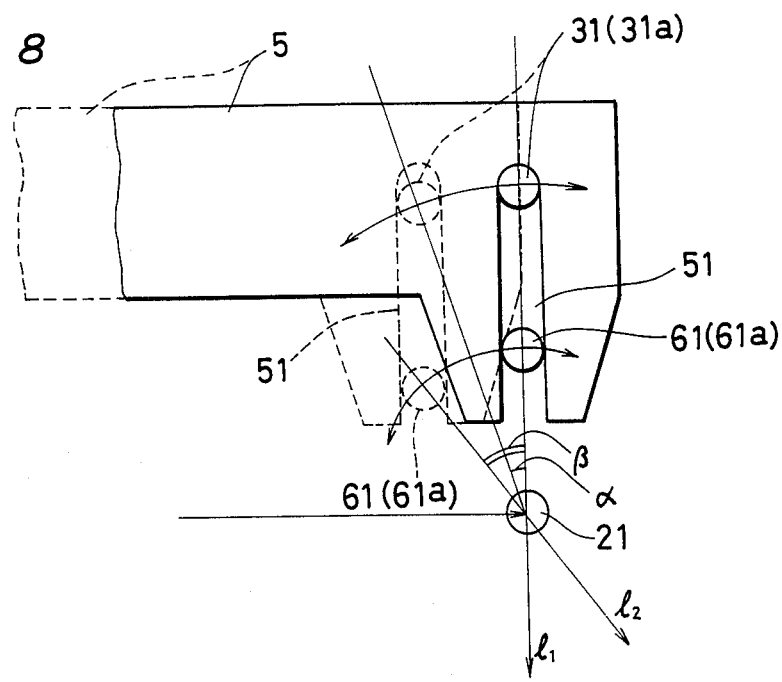
FIG. 8 is a view roughly illustrating the mechanism of the embodiments shown in FIGS. 4 and 7.

As shown in FIGS. 4 to 6, the pivot shaft 21 is pivotably supported at the front end of the support arms 11, 11 which are laterally extended from the handpiece 1 so that the reflector holding member 30 and the applicator holding member 6 are rotatably supported by the pivot shaft 21. At the front end of the slide member 5, a hole for a shaft or slot 51 (a hole for a shaft is shown) which intersects with the axis of the slide member 55 at right angle is provided. In addition, pins 31a and 61a parallel to the pivot shaft 21 are fixed to the reflector holding member 30 and the applicator holding member 6, and these pins function as the above-mentioned connection points 31 and 61 and are fitted into the shaft hole 51. The distance from the pin 31a to the pivot 21 is twice as large as that from the pin 61a to the pivot shaft 21. With this structure, when the slide member 5 is slid backward as shown in FIG. 8, the pins 31a and 61a are moved by the hole 51 and turn counterclockwise around the pivot shaft 21 while the pins 31a and 61a slide in the longitudinal direction of the hole 51. At this time, the reflected (refracted) light $l_1$ of the laser beam changes to the reflected light $l_2$. Since the rotation angle $\beta$ of the pin 61a is approximately twice as large as the rotation angle $\alpha$ of the pin 31a, the probe 60 and the related parts mounted on the applicator holding member 6 are almost accurately aligned with the optical path of the reflected light $l_2$. This is because the angle of the reflected light changes twice as much as the angle of the reflector 3 when the reflector 3 is turned to refract incident light irradiated in a fixed direction. In FIG. 4, the laser beam is refracted at an almost right angle. The surface of the reflector 3 faces the end of the optical fiber 7 at an angle of 45 degrees and the probe 60 and the related parts are provided at an angle of almost 90 degrees to the axis of the handpiece body 1 so that the reflected light $l_1$ of the laser beam is emitted at an angle of almost 90 degrees to the incident light. When the slide member 5 is slid backward by moving the sleeve 4 backward, the reflector holding member 30 and the applicator holding member 6 turn counterclockwise around the pivot shaft 21 as shown in FIG. 6. At this time, the change of angle of the applicator holding member 6 is twice as large as that of the reflector holding member 30. Therefore, the reflected light $l_2$ of the laser beam passes through the contact treatment probe 60 mounted on the applicator holding member 6 and is used for contact treatment. According to the above description, it is easily understood that the laser beam can also be refracted in the direction opposite to the above-mentioned direction by moving the sleeve 4 forward. Referring to FIG. 7, the pivot shaft 21 is supported by the head housing 20 screwed into the handpiece body 1. The reflector holding member 30 and the applicator holding member 6 are covered with the housing 20. In the case of the embodiment shown in FIGS. 4 to 6, the reflector holding member 30 and the applicator holding member 6 can be maintained and checked easily. However, since these holding members 30 and 6 are exposed, their surfaces must be smooth (their edges must be rounded) to prevent a mouth wall from being injured when the handpiece is inserted into a mouth for medical treatment. The reflector holding member 30 and the applicator holding member 6 of the handpiece shown in FIG. 7, however, are covered with the housing 20. It is not necessary to smoothen their surfaces. Furthermore, the holding members 30 and 6 are far less likely to be damaged or contaminated. The structures and functions of other members of this embodiment are similar to those of the above-mentioned embodiment and are not detailed here.

Numeral 7 in FIGS. 4, 6 and 7 designate an optical fiber used to transmit the laser beam. The optical fiber 7, covered with a sheath 71 and connected to a laser source (not shown), is inserted into the body 1 coaxially with the axis of the body 1. The end of the optical fiber 7 faces the reflector 30 at the head section 2. Numeral 8 designates an outlet provided to discharge an active medium such as water or medicine required for dental treatment. The outlet 8 is secured to the slide member 5 and moves back and forth as the slide member 5 is slid. The active medium supplied through a supply passage 81 is jetted from the outlet to a treatment portion.

Figure 9:
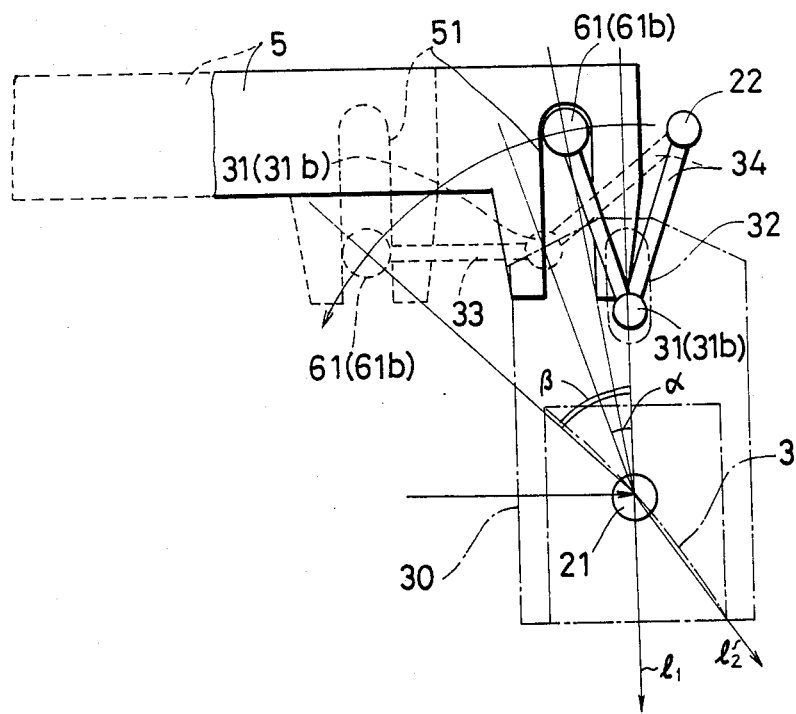
FIG. 9 is a view roughly illustrating the mechanism of a fourth embodiment.

FIG. 9 is a view roughly illustrated the mechanism of a fourth embodiment of the present invention. In the case of this embodiment, a pivot shaft 22 is fixed to the head section 2, a pin 61b is also fixed to the upper section of the applicator holding member 6, and links 33 and 34, having an identical length, are provided between the pin 61b and the pivot shaft 22 and connected to each other so that the angle between the links can be changed via the connection pin 31b. The pin 61b is fitted into a vertical hole for a shaft or slot 51 formed at the end of the slide member 5, and the connection pin 31b is slidably fitted into a slot 32 provided along the axis of the reflector member 30. In this case, the connection pin 31b and the pin 61b actually function as the above-mentioned connection points 31 and 61. When the slide member 5 is slid backward as shown by the broken lines in FIG. 9, the pin 61b is pulled backward and turned around the pivot shaft 21 via the hole 51. The pin 31b thus slides in the slot 32 and turns around the pivot shaft 21. Consequently, both the reflector holding member 30 and the applicator holding member 6 turn around the pivot shaft 21. At this time, the pin 31b is always positioned on the midline of the isosceles triangle formed by the pin 61b, the pivot shaft 21 and the pivot shaft 22. Therefore, the change of the angle $\beta$ of the pin 61b is approximately twice as large as the change of the angle $\alpha$ of the pin 31b. Accordingly, the change of angle of the applicator holding member 6 is twice as large as that of the reflector holding member 30 and the probe 60 and the related parts are properly aligned with the optical path of the reflected light.

As described above, in the case of the laser-type handpieces of the present invention shown in FIGS. 4 to 9, the angle of the reflector holding member 30 pivotably connected to the head 2 can be changed by moving the control sleeve 4, which is fitted over the external circumference of the handpiece body 1, back and forth along the axis of the body 1. With this structure, the members which are used to change the angle of the reflector holding member 3 do not protrude outside the head section 2. When the handpiece is applied to a dental handpiece, it can be inserted into and taken out from a narrow oral region without problems. The irradiation direction of the laser beam can be changed during treatment by operating the sleeve 4 which is provided away from the head section 2. Therefore, it is not necessary to take out the head section 2 from the mouth each time the irradiation angle is changed. This ensures efficient and accurate treatment. Furthermore, since the applicator holding member 6 of the present invention rotates together with the reflector holding member 30 and the applicator mounted on the applicator holding member 6 is properly aligned with the optical path of the reflected light of the laser beam at all times, the angle of the laser beam can be changed as desired during treatment. As a result, the characteristics of the laser beam can be fully utilized. Accordingly, the members peripheral to the handpiece can be made more compact.

I claim:

1. A laser-type handpiece wherein a laser beam transmitted from a laser source to a handpiece body is refracted at a head section, said laser-type handpiece is characterized in that said handpiece comprises a reflector holding member and an applicator holding member pivotally connected to said head section via a pivot shaft, a control sleeve fitted over the external circumference of said body so that said sleeve can be moved back and forth along the axis of said body, and a slide member which is connected to an upper section of said reflector holding member and an upper section of said applicator holding member via connection points and is provided in said body so that said slide member can slide along the axis of said body, and is interlocked with the back-and-forth movement of said sleeve, whereby said reflector holding member and said applicator holding member are turned around said pivot shaft by sliding said slide member interlocked with the back-and-forth movement of said sleeve and the change of angle of said applicator holding member is approximately twice as large as that of said reflector holding member.

2. A laser-type handpiece according to claim 1, wherein an optical fiber for laser beam transmission is built in said handpiece body and the end of said optical fiber faces said reflector.

3. A laser-type handpiece according to claim 1, wherein pins are fixed to said upper sections of said reflector holding member and said applicator holding member respectively, a shaft hole or slot is provided at the front end of said slide member, and pins are fitted into said shaft hole or slot and the distance from said pin to said pivot shaft is twice as large as that from said pin to said pivot shaft.

4. A laser-type handpiece according to claim 1, wherein a pivot shaft is fixed to said head section, a pin is also fixed to said upper section of said applicator holding member, links having an identical length, are provided between said pin and said pivot shaft and connected to each other via a connection pin so that the angle between said links can be changed, said pin is fitted into said shaft hole or slot formed at said front end of said slide member, and said connection pin is slidably fitted into a slot provided along the axis of said reflector member.

5. A laser-type handpiece according to claim 1, wherein an optical fiber for laser beam transmission is built in said handpiece body and the end of said optical fiber faces said reflector holding member.

* * * * *